(12) United States Patent
Chung

(10) Patent No.: US 9,107,987 B2
(45) Date of Patent: Aug. 18, 2015

(54) IRRIGATOR PORT FOR PHLEGM SUCTION TUBE

(75) Inventor: Donny Chung, Taipei (TW)

(73) Assignee: PACIFIC HOSPITAL SUPPLY CO., LTD., Taipei (TW)

(*) Notice: Subject to any disclaimer, the term of this patent is extended or adjusted under 35 U.S.C. 154(b) by 287 days.

(21) Appl. No.: 13/204,885

(22) Filed: Aug. 8, 2011

(65) Prior Publication Data

US 2013/0041313 A1  Feb. 14, 2013

(51) Int. Cl.
*A61M 39/10* (2006.01)
*A61M 1/00* (2006.01)
*A61M 39/24* (2006.01)
*A61M 39/26* (2006.01)

(52) U.S. Cl.
CPC ....... *A61M 1/008* (2013.01); *A61M 2039/1033* (2013.01); *A61M 2039/2473* (2013.01); *A61M 2039/263* (2013.01); *A61M 2209/10* (2013.01)

(58) Field of Classification Search
CPC . A61M 39/12; A61M 39/06; A61M 39/1011; A61M 39/20; A61M 2039/1033; A61M 2039/20; A61M 2039/26; A61M 2039/261; A61M 2039/2473
USPC .......... 604/31, 30, 33, 34, 533, 537–539, 905
See application file for complete search history.

(56) References Cited

U.S. PATENT DOCUMENTS

| | | | |
|---|---|---|---|
| 2,117,296 A * | 5/1938 | Cahoon | 222/153.13 |
| 3,185,355 A * | 5/1965 | Lipman | 222/341 |
| 3,332,585 A * | 7/1967 | Cox | 222/309 |
| 3,710,942 A * | 1/1973 | Rosenberg | 210/136 |
| 4,278,189 A * | 7/1981 | Kirk, Jr. | 222/321.2 |
| 4,437,588 A * | 3/1984 | Shay | 222/321.2 |
| 4,681,571 A * | 7/1987 | Nehring | 604/320 |
| 4,917,668 A * | 4/1990 | Haindl | 604/167.03 |
| 5,029,580 A * | 7/1991 | Radford et al. | 128/207.14 |
| 5,261,883 A * | 11/1993 | Hood et al. | 604/153 |
| 5,365,970 A * | 11/1994 | Butler | 137/192 |
| 5,390,898 A * | 2/1995 | Smedley et al. | 251/149.6 |
| 5,575,767 A * | 11/1996 | Stevens | 604/505 |
| 5,993,402 A * | 11/1999 | Sauer et al. | 601/162 |
| 6,030,215 A * | 2/2000 | Ellion et al. | 433/89 |
| 6,354,312 B1 * | 3/2002 | Lin et al. | 134/169 C |
| 6,460,560 B1 * | 10/2002 | Weinheimer et al. | 137/232 |
| 6,755,650 B2 * | 6/2004 | Decosterd et al. | 433/88 |
| 7,988,657 B2 * | 8/2011 | Shapiro et al. | 604/27 |
| 2003/0077552 A1* | 4/2003 | Decosterd et al. | 433/84 |
| 2004/0209222 A1* | 10/2004 | Snyder et al. | 433/80 |
| 2006/0272120 A1* | 12/2006 | Barrick et al. | 15/321 |
| 2007/0105065 A1* | 5/2007 | Snyder et al. | 433/89 |
| 2008/0033371 A1* | 2/2008 | Updegraff et al. | 604/263 |
| 2008/0234639 A1* | 9/2008 | Antonio et al. | 604/249 |

* cited by examiner

Primary Examiner — Aarti B Berdichevsky
(74) Attorney, Agent, or Firm — Chun-Ming Shih; HDLS IPR Services (57) ABSTRACT

A tube coupling of a phlegm suction tube, which is capable of connecting two injectors having different mating structures, includes a tube body and a tube connector. The tube body is hollow and has a coupling end and a check valve. The tube connector is coaxially connected to the coupling end of the tube body and has a joint portion. The joint portion has a passage communicating with the tube body. The check valve flexibly closes the passage from the tube body. A diameter of the passage fits a first injector with a first mating structure, and an outer diameter of the joint portion fits a second injector with a second mating structure.

9 Claims, 8 Drawing Sheets

IRRIGATOR PORT FOR PHLEGM SUCTION TUBE

BACKGROUND OF THE INVENTION

1. Technical Field

The invention relates to medical appliances, particularly to phlegm suckers.

2. Related Art

Figure 1:
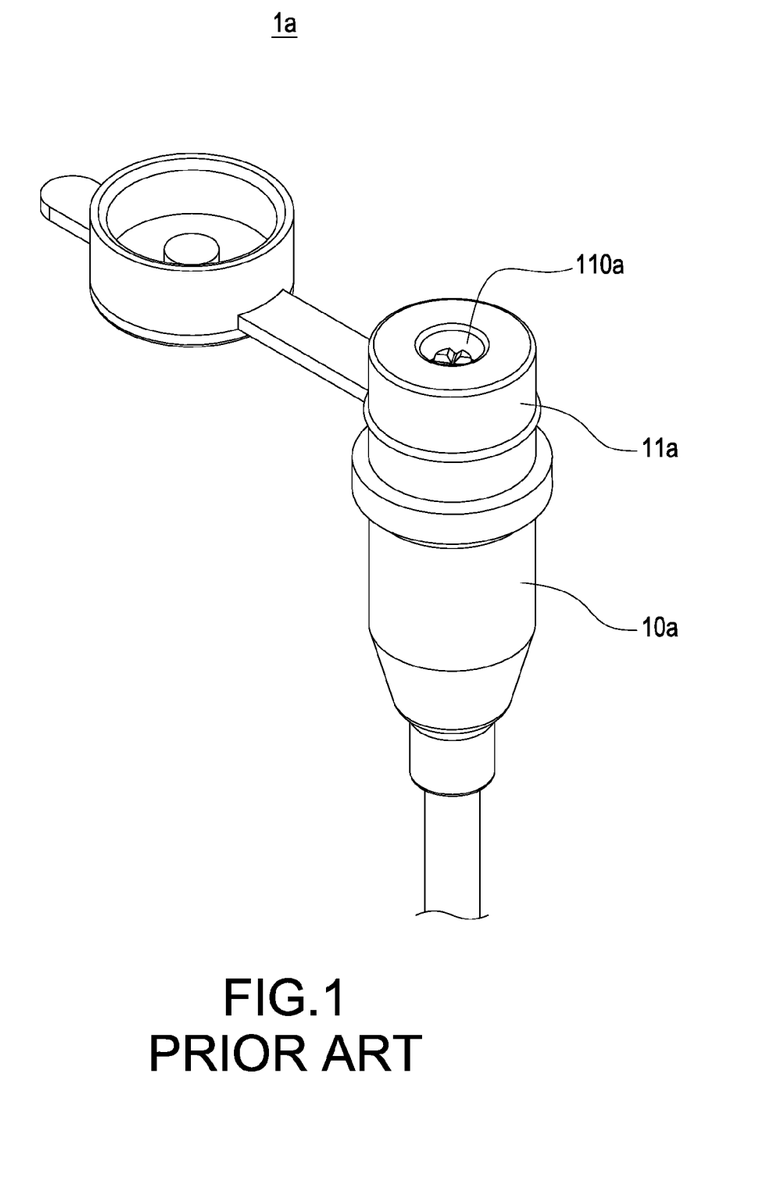
FIG. 1 shows a conventional irrigator port.

A conventional irrigator port 1a is shown in FIG. 1. The irrigator port 1a includes a tube body 10a and a tube connector 11a connecting to one end of the tube body 10a. A passage 110a is formed in the tube connector 11a and communicates with the tube body 10a. One end of the tube body 10a may be connected to a phlegm suction tube. The tube body 10a is provided with a check valve which flexibly closes the passage 110a for preventing phlegm from flowing back and allowing to inject chemical agents, such as cleaners and germicides, through the passage 110a. Usually, injecting chemical agents is performed by inserting a syringe into the passage 110a.

However, the passage 110a of the coupling 1a can fit an injector with a specific single size. Usually, a diameter of the passage 110a is about 3.85 mm-3.90 mm. Those injectors with sizes other than this size cannot be fit. This causes a restriction of usability. Besides, the irrigator port 1a cannot be changed into another size.

SUMMARY OF THE INVENTION

An object of the invention is to provide a tube coupling of a phlegm suction tube, which can fit two injectors having different mating structures. This will increase availability of injectors.

To accomplish the above object, the irrigator port of the invention includes a tube body and a tube connector. The tube body is hollow and has a coupling end and a check valve. The tube connector is coaxially connected to the coupling end of the tube body and has a joint portion. The joint portion has a passage communicating with the tube body. The check valve flexibly closes the passage from the tube body. A diameter of the passage fits a first injector with a first mating structure, and an outer diameter of the joint portion fits a second injector with a second mating structure.

DETAILED DESCRIPTION OF THE INVENTION

Figure 2:
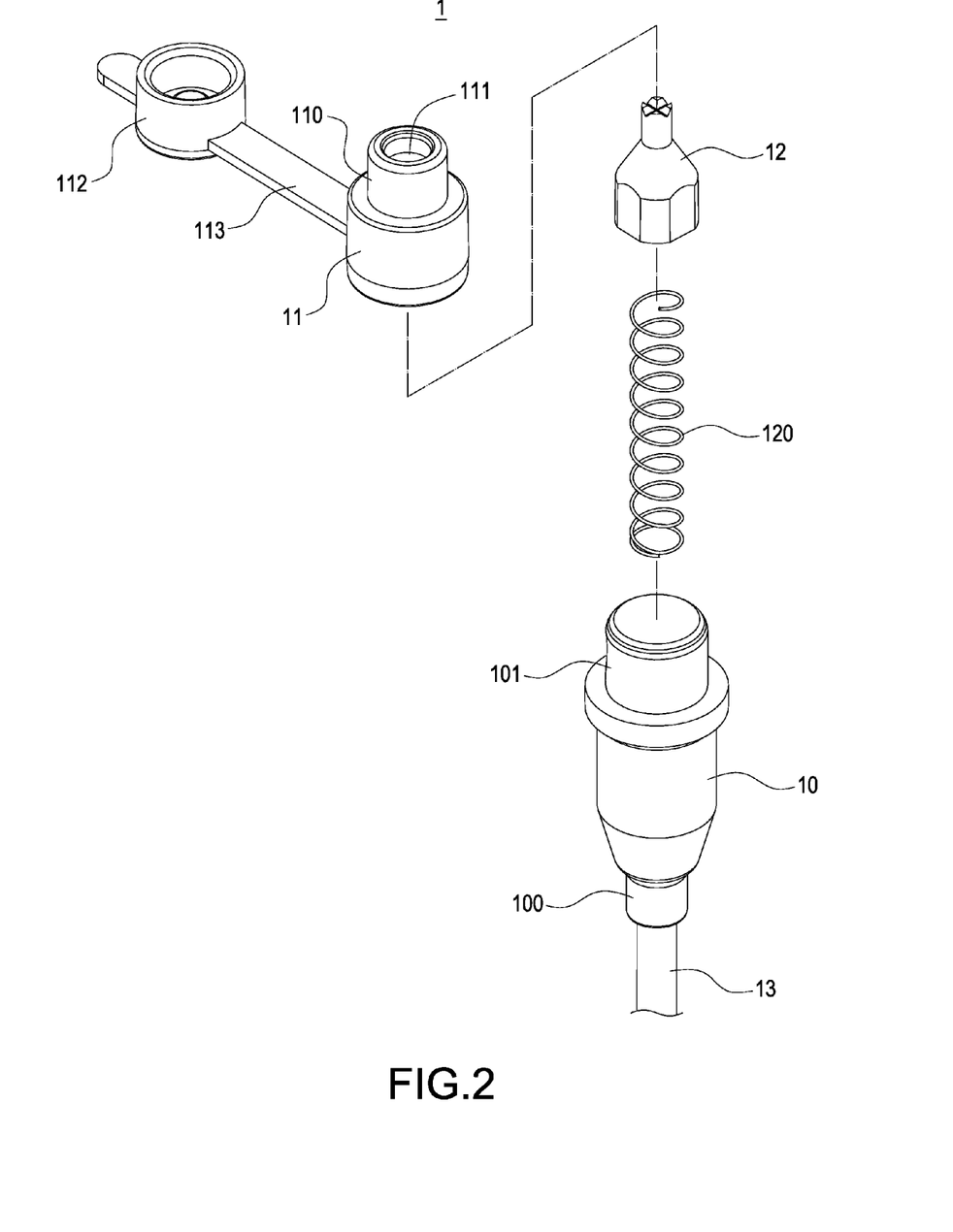
FIG. 2 is an exploded view of the invention.
Figure 3:
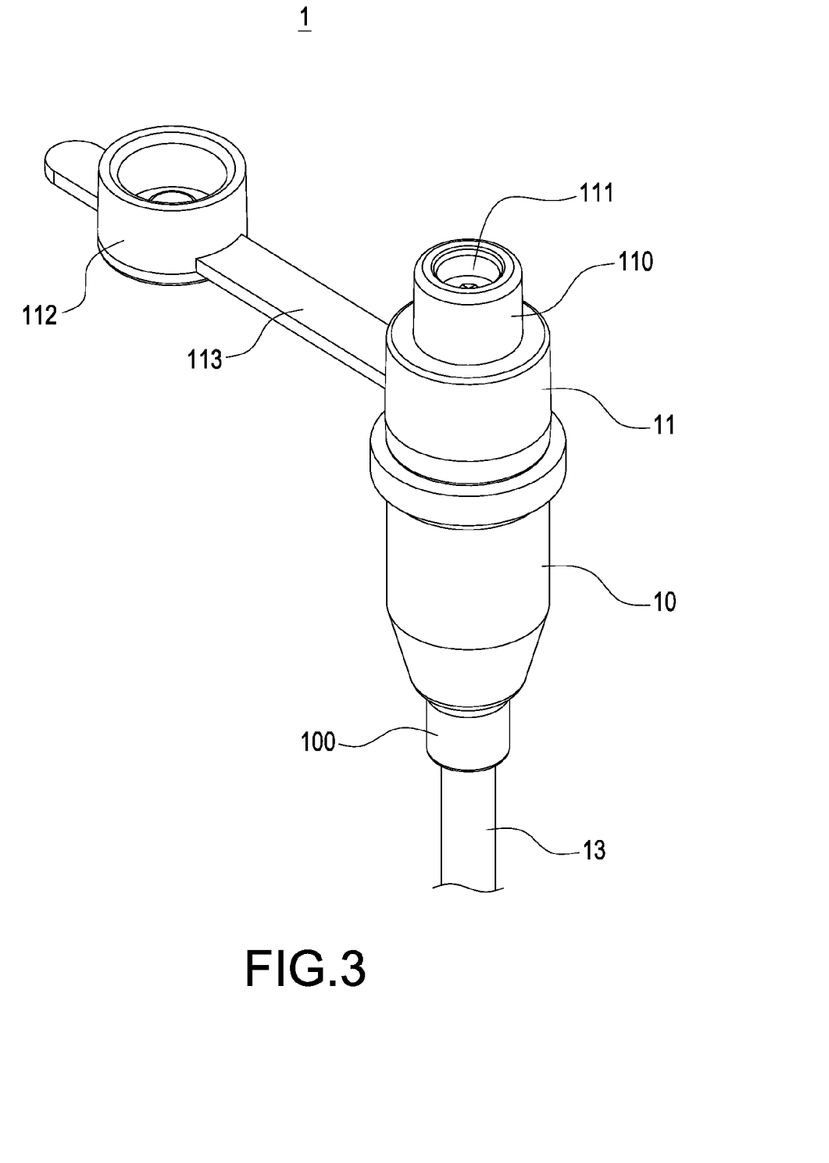
FIG. 3 is an assembled view of the invention.
Figure 6:
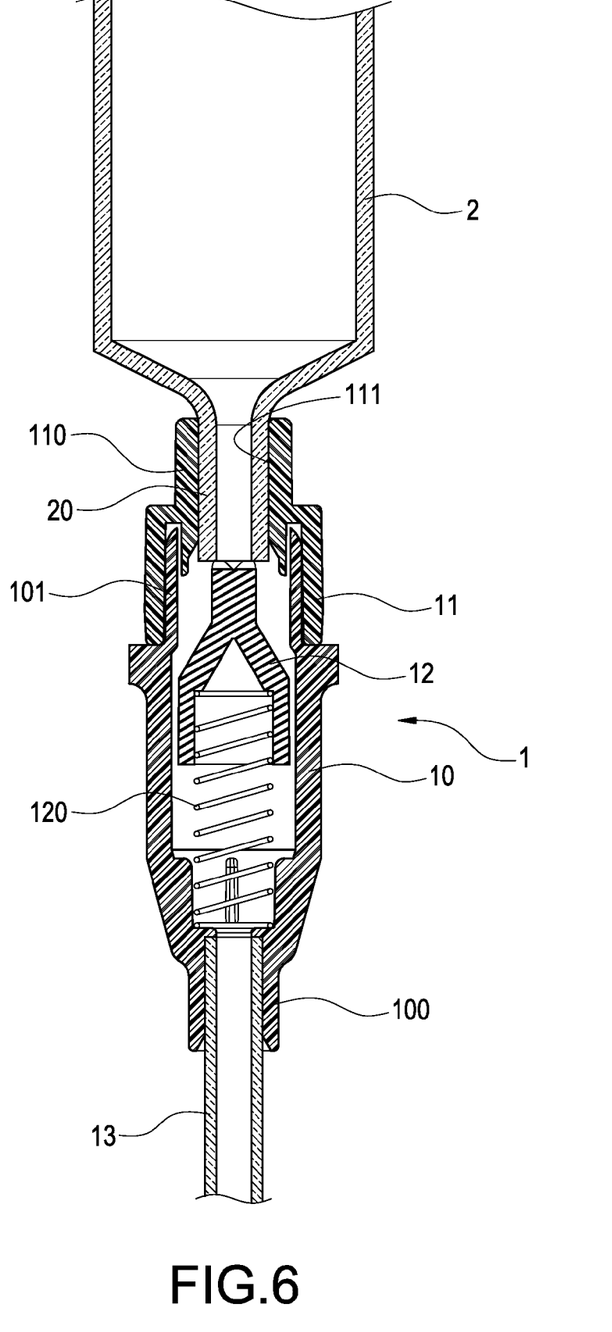
Figure 8:
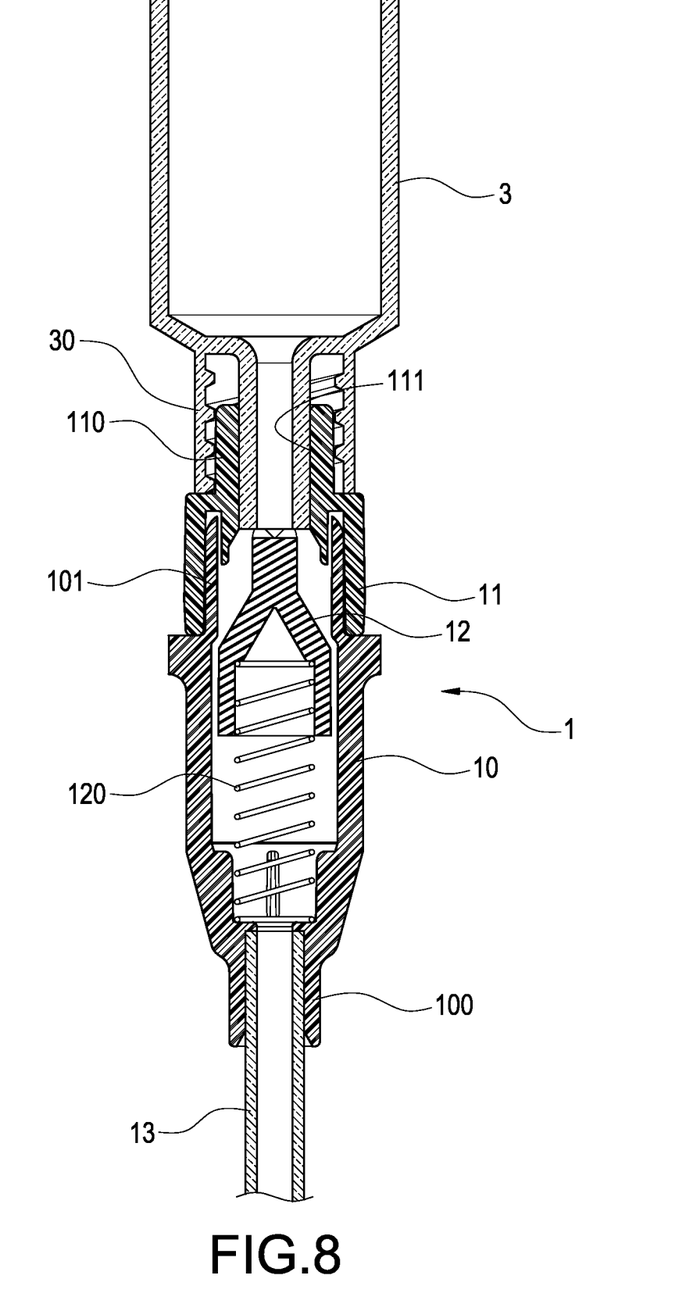

Please refer to FIGS. 2 and 3. The irrigator port of the invention is capable of connecting two injectors 2, 3 having different mating structures as shown in FIGS. 6 and 8 for increase of availability. The irrigator port 1 includes a tube body 10 and a tube connector 11.

The tube body 10 is of a hollow shape and has a connecting end 100 and a coupling end 101. The connecting end 100 and the coupling end 101 communicate with each other. A check valve 12 is disposed in the tube body 10. The connecting end 100 is used for connecting a tube 13 which extends to a phlegm suction tube (not shown).

Figure 4:
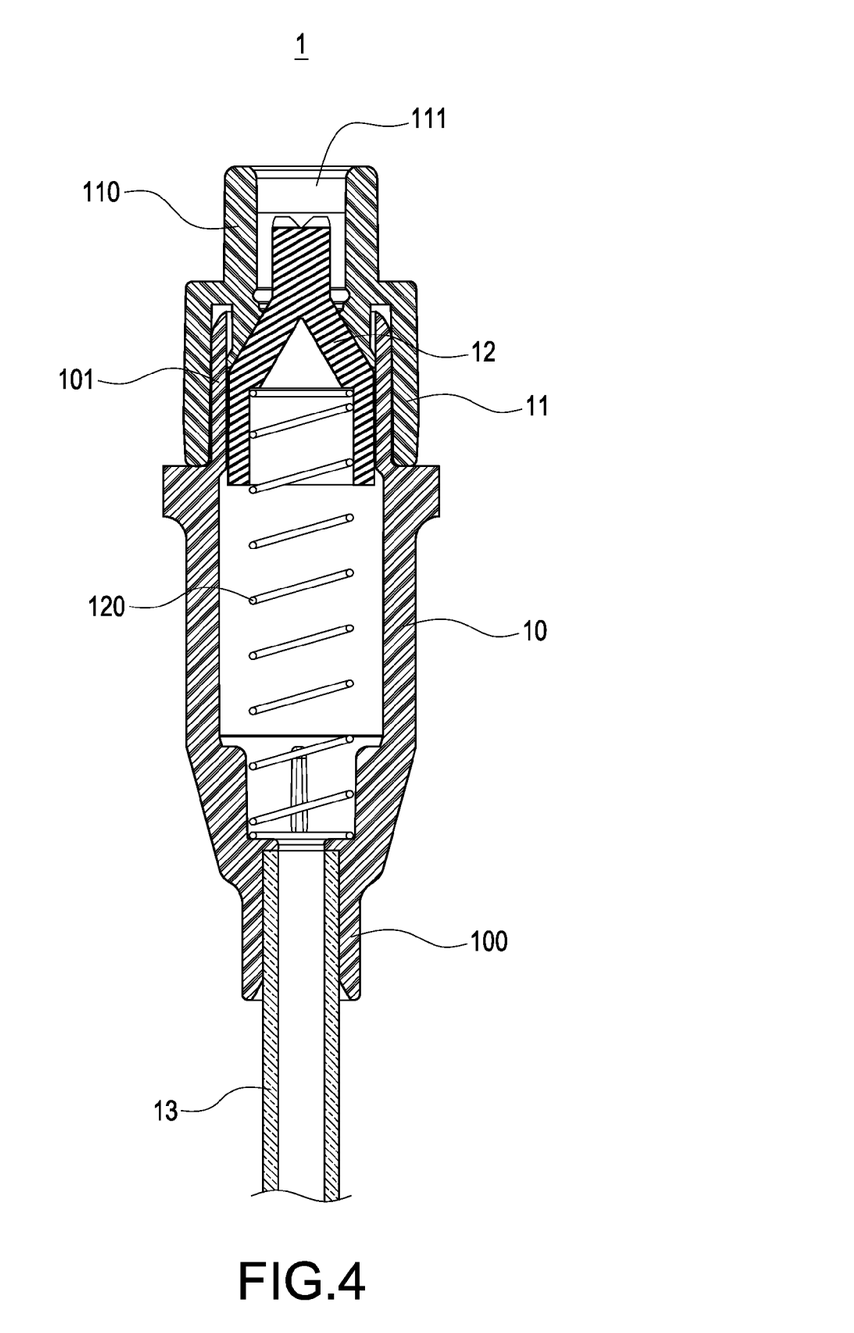
FIG. 4 is a cross-sectional view of the invention.

The tube connector 11 is tightly connected to the coupling end 101 of the tube body 10 and has a joint portion 110 with a step shape (i.e. the outer portion is smaller in size). The joint portion 110 is formed with a passage 111 therein. The passage 111 can communicate with the hollow of the tube body 10 and the check valve 12 flexibly closes the passage 111 as shown in FIG. 4 when the tube connector 11 is connected onto the coupling end 101. In the shown embodiment, the check valve 12 is elastically pushed by a spring 120 so that the check valve 12 can normally close the passage 111 when no other force is applied. Besides, the joint portion 110 of the tube connector 11 may be covered by a cap 112. The cap 112 may be connected by a flexible connecting element 113 extending from the tube connector 11. The joint portion 110 may be cloaked by the cap 112 for protection when not in use.

Figure 5:
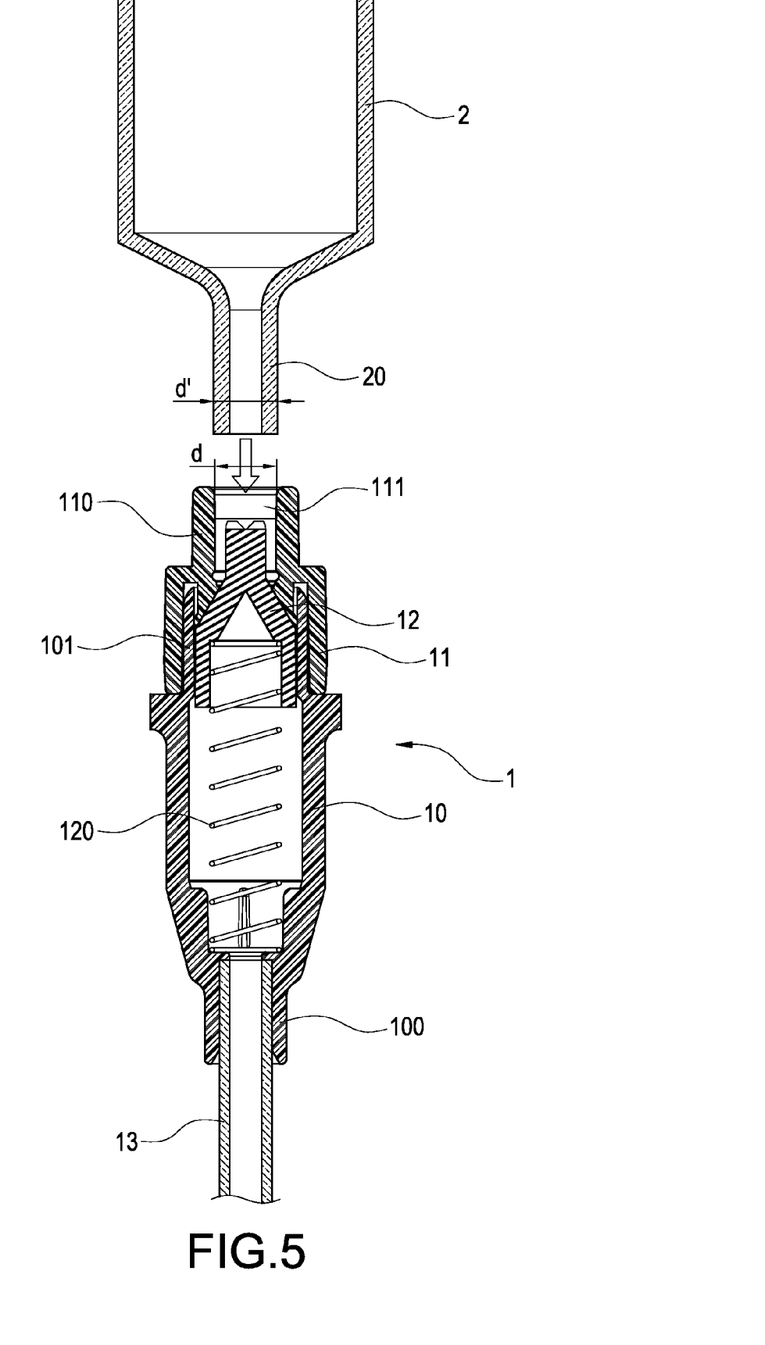
FIGS. 5 and 6 show how the invention is connected by a first injector having a first mating structure.

Please refer to FIGS. 5 and 6. The diameter d of the passage 111 is about from 3.85 mm to 3.90 mm. The injector 2 is provided with a nozzle 20 whose diameter can fit that of the passage 111. Accordingly, the nozzle 20 can be connected into the passage 111 and then push the check valve 12 to open the passage 111 so that a chemical agent in the injector 2 can be injected into the irrigator port 1.

Figure 7:
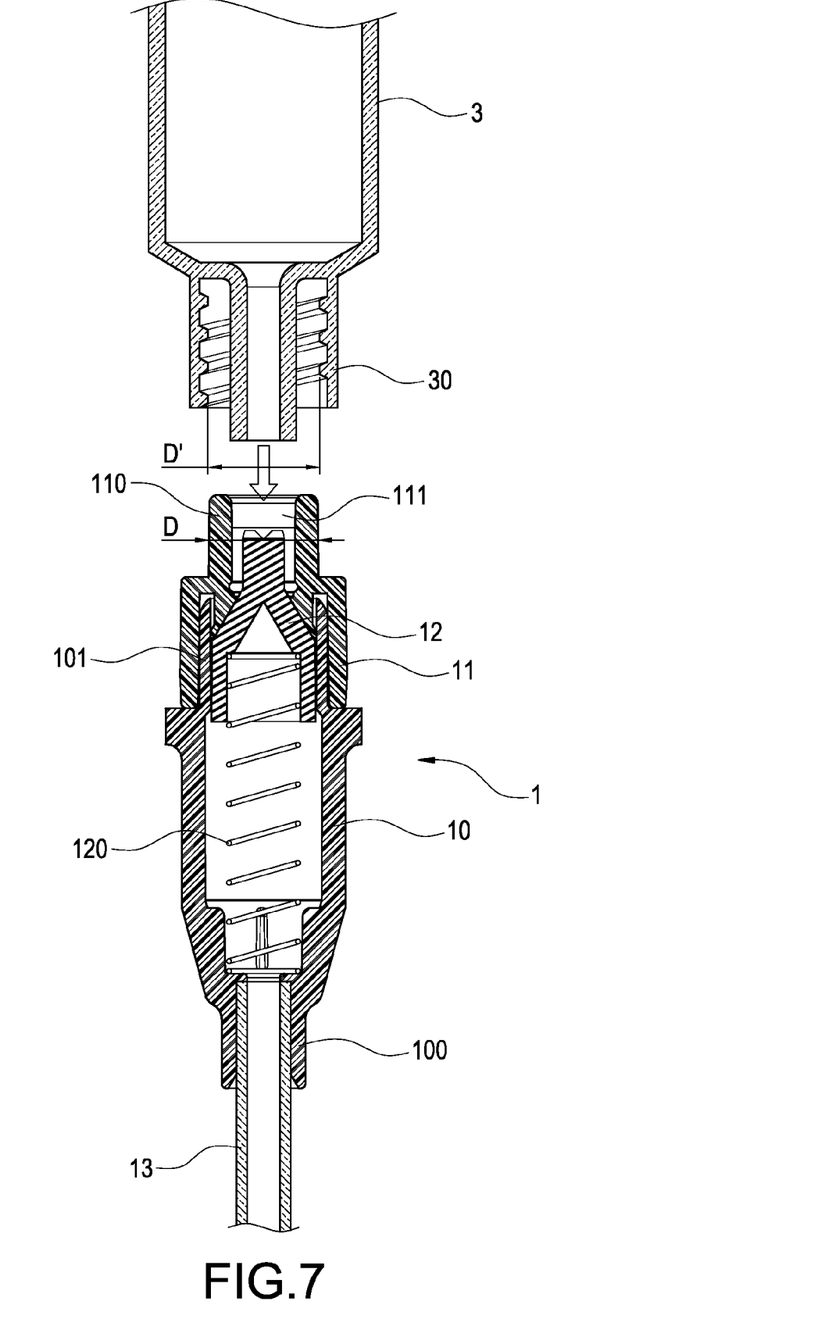
FIGS. 7 and 8 show how the invention is connected by a second injector having a second mating structure.

Please further refer to FIGS. 7 and 8. An outer diameter D of the joint portion 110 is about 6.5 mm to 7 mm and able to connect another injector 3 with different size. The injector 3 is provided with a nozzle 30 whose diameter can fit that of the joint portion 110. Accordingly, the nozzle 30 can be connected into the joint portion 110 and then push the check valve 12 to open the passage 111 so that a chemical agent in the injector 3 can also be injected into the irrigator port 1.

Hence, two injectors 2, 3 having different mating structures can be used to connect the irrigator port 1. In other words, the injector, which can fit the irrigator port 1, is not restricted to only one mating structure any longer.

While the forgoing is directed to an embodiment of the present invention, other and further embodiments of the invention may be devised without departing from the basic scope thereof. As such, the appropriate scope of the invention is to be determined according to the claims.

What claimed is:

1. An irrigator port for a phlegm suction tube to fit two injectors having different mating structures, comprising:
    a tube body, being hollow, a coupling end being formed at one end of the tube body and a connecting end being formed at the other end of the tube body;
    a check valve having a valve head protruding out of the coupling end after the check valve is disposed in the coupling end, wherein the valve head is formed at one end of the check valve, and a recess is formed at the other end of the check valve;
    a spring with one end disposed inside the recess so that the check valve is elastically pushed by the spring; and
    a tube connector, coaxially connected to the coupling end of the tube body, having a joint portion surrounding the valve head, wherein the joint portion has a passage communicating with the tube body, and the check valve flexibly closes the passage from the tube body;
    wherein a diameter of the passage fits a first injector with a first mating structure, and an outer diameter of the joint portion fits a second injector with a second mating structure, and
    wherein after a nozzle of the first injector or the second injector is engaged with the tube connector to push the valve head out of the passage and being located inside the tube body, a chemical agent in the first injector or the second injector flows out of the nozzle and around an outer surface of the check valve towards the connecting end.

2. The irrigator port of claim 1, wherein the connecting end is used to connect a tube.

3. The irrigator port of claim 1, wherein an outer diameter of the joint portion is about between 6.5 mm and 7 mm.

4. The irrigator port of claim 1, wherein the joint portion is of a step shape.

5. The irrigator port of claim 1, further comprising a cap for cloaking the joint portion.

6. The irrigator port of claim 5, wherein the cap is connected to the tube connector by a flexible connecting element.

7. The irrigator port of claim 1, wherein a diameter of the passage is about between 3.85 mm and 3.90 mm.

8. The irrigator port of claim 7, wherein an outer diameter of the joint portion is about between 6.5 mm and 7 mm.

9. The irrigator port of claim 8, wherein the joint portion is of a step shape.

\* \* \* \* \*